(12) United States Patent
Tenger et al.

(10) Patent No.: US 8,968,186 B2
(45) Date of Patent: Mar. 3, 2015

(54) HANDLE FOR FIBER OPTIC DEVICE

(75) Inventors: James P. Tenger, Carlsbad, CA (US);
John R. Hicks, Carlsbad, CA (US)

(73) Assignee: Intubrite, LLC, Vista, CA (US)

( * ) Notice: Subject to any disclaimer, the term of this patent is extended or adjusted under 35 U.S.C. 154(b) by 369 days.

(21) Appl. No.: 13/599,995

(22) Filed: Aug. 30, 2012

(65) Prior Publication Data

US 2012/0330104 A1    Dec. 27, 2012

Related U.S. Application Data

(63) Continuation-in-part of application No. 13/328,499, filed on Dec. 16, 2011, which is a continuation-in-part of application No. 13/290,792, filed on Nov. 7, 2011, now abandoned, which is a continuation of application (Continued)

(51) Int. Cl.
*A61B 1/267* (2006.01)
*A61B 1/07* (2006.01)
*A61B 1/06* (2006.01)

(Continued)

(52) U.S. Cl.
CPC ............... *A61B 1/07* (2013.01); *A61B 1/0684* (2013.01); *A61B 1/2673* (2013.01); *A61B 1/043* (2013.01); *A61B 1/0638* (2013.01); *A61B 1/267* (2013.01); *A61M 16/04* (2013.01)
USPC .......................................... 600/199; 600/245

(58) Field of Classification Search
CPC ..... A61B 1/267; A61B 1/0669; A61B 1/0661
USPC .......................................... 600/185–200, 245
See application file for complete search history.

(56) References Cited

U.S. PATENT DOCUMENTS

D185,398 S     6/1959  Todt
3,592,199 A *  7/1971  Ostensen ...................... 600/198

(Continued)

FOREIGN PATENT DOCUMENTS

KR    1020070044379     4/2007
WO    WO93/01170        6/1993

OTHER PUBLICATIONS

Notification, International Search Report and Written Opinion dated Feb. 8, 2013 from PCT/US2012/63972.

(Continued)

*Primary Examiner* — Eduardo C Robert
*Assistant Examiner* — Stuart S Bray
(74) *Attorney, Agent, or Firm* — Stephen C. Beuerle; Procopio Cory Hargreaves & Savitch LLP

(57) ABSTRACT

A laryngoscope handle for use with a fiber optic laryngoscope blade having fiber optics includes a laryngoscope handle body configured to be gripped by a handle of a user; one or more power sources carried by the handle body; a light source assembly carried by the handle body and powered by the one or more power sources; a connection section for mechanically connecting the fiber optic laryngoscope blade to the laryngoscope handle and optically coupling the light source assembly in the laryngoscope handle to the fiber optics of the fiber optic laryngoscope blade, wherein the light source assembly includes at least two different types of light sources and a light mixing chamber where light emitted from the two different types of light sources mix to create a combined, mixed light that is transmitted to the fiber optics of the fiber optic laryngoscope blade for emission there from.

13 Claims, 1 Drawing Sheet

Related U.S. Application Data

No. 12/698,467, filed on Feb. 2, 2010, now Pat. No. 8,152,719, which is a continuation-in-part of application No. 29/346,594, filed on Nov. 3, 2009, now Pat. No. Des. 632,787, application No. 13/599,995, which is a continuation-in-part of application No. 12/368,952, filed on Feb. 10, 2009, now abandoned, which is a continuation-in-part of application No. 12/173,961, filed on Jul. 16, 2008, now Pat. No. 8,012,087, which is a continuation-in-part of application No. 12/144,147, filed on Jun. 23, 2008, now Pat. No. 8,257,250.

(51) Int. Cl.
*A61B 1/04* (2006.01)
*A61M 16/04* (2006.01)

(56) References Cited

U.S. PATENT DOCUMENTS

| | | | |
|---|---|---|---|
| 3,863,627 A | 2/1975 | Bouffard | |
| 3,976,054 A | 8/1976 | Evans | |
| 4,380,790 A | 4/1983 | Saferstein et al. | |
| D271,135 S | 10/1983 | Greenblatt | |
| 4,583,528 A * | 4/1986 | Bauman | 600/199 |
| 4,694,822 A * | 9/1987 | Bauman | 600/198 |
| 4,729,367 A * | 3/1988 | Bauman | 600/198 |
| D297,363 S | 8/1988 | Salerno et al. | |
| 4,782,819 A | 11/1988 | Adair | |
| 4,827,910 A | 5/1989 | Mathews, III | |
| 5,165,387 A | 11/1992 | Woodson | |
| D337,384 S | 7/1993 | Schucman | |
| 5,645,116 A | 7/1997 | McDonald | |
| 5,707,135 A | 1/1998 | Miller, Jr. | |
| 5,868,775 A | 2/1999 | Bircoll | |
| 6,102,851 A * | 8/2000 | Mellin | 600/199 |
| 6,135,948 A * | 10/2000 | Lee | 600/189 |
| D449,499 S | 10/2001 | Voges | |
| 6,459,919 B1 | 10/2002 | Lys et al. | |
| 6,569,089 B1 | 5/2003 | Covington et al. | |
| D491,267 S | 6/2004 | Ashraf | |
| 6,809,499 B2 | 10/2004 | Solingen | |
| 6,876,446 B2 | 4/2005 | Taylor et al. | |
| D512,778 S | 12/2005 | Ashraf | |
| 6,974,239 B2 | 12/2005 | Currie et al. | |
| 7,052,456 B2 | 5/2006 | Simon | |
| D541,937 S | 5/2007 | Yee | |
| D547,449 S | 7/2007 | Ashraf | |
| D550,841 S | 9/2007 | Berci et al. | |
| D554,255 S | 10/2007 | Iqbal | |
| 7,308,296 B2 | 12/2007 | Lys et al. | |
| D559,982 S | 1/2008 | Iqbal | |
| D581,532 S | 11/2008 | Cranton et al. | |
| 7,824,331 B1 | 11/2010 | Cranton et al. | |
| 7,878,973 B2 * | 2/2011 | Yee et al. | 600/199 |
| 8,114,015 B2 * | 2/2012 | Ayoun et al. | 600/199 |
| 8,142,353 B2 * | 3/2012 | Pecherer et al. | 600/199 |
| 8,152,719 B2 * | 4/2012 | Tenger et al. | 600/199 |
| 8,162,826 B2 * | 4/2012 | Pecherer et al. | 600/197 |
| 8,317,693 B2 * | 11/2012 | Grey et al. | 600/212 |
| 2002/0038075 A1 * | 3/2002 | Tsai | 600/200 |
| 2002/0087050 A1 | 7/2002 | Rudischhauser et al. | |
| 2003/0121521 A1 | 7/2003 | Hipolito et al. | |
| 2003/0191459 A1 | 10/2003 | Ganz et al. | |
| 2003/0195390 A1 | 10/2003 | Graumann | |
| 2004/0039252 A1 | 2/2004 | Koch | |
| 2004/0150989 A1 | 8/2004 | Burke et al. | |
| 2004/0240204 A1 | 12/2004 | Russ et al. | |
| 2005/0043591 A1 * | 2/2005 | Witte | 600/200 |
| 2005/0054903 A1 | 3/2005 | Cantrell | |
| 2005/0159649 A1 | 7/2005 | Patel | |
| 2006/0030880 A1 | 2/2006 | Tylke | |
| 2006/0069314 A1 | 3/2006 | Farr | |
| 2006/0189847 A1 * | 8/2006 | Yee et al. | 600/199 |
| 2006/0241347 A1 | 10/2006 | Whitehead | |
| 2007/0112257 A1 | 5/2007 | Hensler | |
| 2007/0156022 A1 | 7/2007 | Patel | |
| 2007/0183145 A1 | 8/2007 | Yu | |
| 2007/0232862 A1 | 10/2007 | Herman | |
| 2007/0276185 A1 | 11/2007 | Gono et al. | |
| 2007/0276191 A1 | 11/2007 | Selover et al. | |
| 2007/0287961 A1 | 12/2007 | Parker | |
| 2008/0015560 A1 | 1/2008 | Gowda et al. | |
| 2008/0045800 A2 | 2/2008 | Farr | |
| 2008/0045801 A1 * | 2/2008 | Shalman et al. | 600/193 |
| 2008/0200766 A1 * | 8/2008 | Ayoun et al. | 600/199 |
| 2008/0208006 A1 * | 8/2008 | Farr | 600/178 |
| 2008/0218998 A1 | 9/2008 | Quest et al. | |
| 2008/0300475 A1 | 12/2008 | Jaeger et al. | |
| 2009/0076334 A1 | 3/2009 | Chen | |
| 2009/0099421 A1 * | 4/2009 | Shalman et al. | 600/197 |
| 2009/0187078 A1 | 7/2009 | Dunlop | |
| 2009/0318758 A1 | 12/2009 | Farr et al. | |
| 2010/0022843 A1 * | 1/2010 | Pecherer et al. | 600/197 |
| 2010/0041953 A1 * | 2/2010 | Pecherer et al. | 600/193 |
| 2010/0069722 A1 * | 3/2010 | Shalman et al. | 600/193 |
| 2010/0152541 A1 * | 6/2010 | Tenger et al. | 600/194 |
| 2011/0023885 A1 * | 2/2011 | Vazales et al. | 128/207.14 |
| 2011/0023887 A1 * | 2/2011 | Vazales et al. | 128/207.14 |
| 2011/0130627 A1 | 6/2011 | McGrail et al. | |
| 2012/0041268 A1 * | 2/2012 | Grey et al. | 600/199 |
| 2012/0071725 A1 | 3/2012 | Plevnik et al. | |
| 2012/0078056 A1 * | 3/2012 | Tenger et al. | 600/194 |
| 2012/0330103 A1 * | 12/2012 | Tenger et al. | 600/188 |
| 2014/0012074 A1 * | 1/2014 | Vazales et al. | 600/103 |
| 2014/0033455 A1 * | 2/2014 | Vazales et al. | 15/104.05 |

OTHER PUBLICATIONS

International Search Report and Written Opinion for PCT/US08/074878 dated Mar. 19, 2009, 10 pages.

International Search Report and Written Opinion for PCT/US2010/023194 dated Oct. 5, 2010, 8 pages.

ISO 21348, Space Environment (natural and artificial)—Process for determining solar irradiances, 2007, ISO 21348:2007(E).

International Search Report and Written Opinion for corresponding application No. PCT/US2013/055873, mailed on Nov. 27, 2013 in 13 pages.

Flexicare, BritePro Handle, Internet Wayback Machine capture, http://web.archive.org/web/20110129032344/http://www.flexicare.com/en/products/airway-management/single-patient-use-laryngoscopes/britepro-handle.aspx, Jan. 29, 2011, 3 pages.

* cited by examiner

HANDLE FOR FIBER OPTIC DEVICE

CROSS-REFERENCE TO RELATED APPLICATIONS

This application is a continuation-in-part of U.S. patent application Ser. No. 13/328,499, filed on Dec. 16, 2011, which is a continuation-in-part of U.S. patent application Ser. No. 13/290,792, filed on Nov. 7, 2011, which is a continuation of U.S. patent application Ser. No. 12/698,467, filed Feb. 2, 2010, which is a continuation-in-part of U.S. patent application Ser. No. 29/346,594, filed Nov. 3, 2009, now U.S. Des. Pat. No. D632,787, and is a continuation-in-part of U.S. patent application Ser. No. 12/368,952, filed Feb. 10, 2009, now abandoned, which is a continuation-in-part of U.S. patent application Ser. No. 12/173,961, filed on Jul. 16, 2008, now U.S. Pat. No. 8,012,087, which is a continuation-in-part of U.S. patent application Ser. No. 12/144,147, filed Jun. 23, 2008. This application also claims priority under 35 U.S.C. 119(e) to U.S. Provisional patent application No. 61/288,779, filed Dec. 21, 2009. The contents of each and all of the above patent applications are incorporated herein by reference in their entirety.

FIELD OF THE INVENTION

The field of this invention relates, in general, to illumination devices, and, in particular, to laryngoscope handles for laryngoscope blades.

SUMMARY OF THE INVENTION

An aspect of the invention involves a laryngoscope handle for use with a fiber optic laryngoscope blade including fiber optics. The laryngoscope handle includes a laryngoscope handle body configured to be gripped by a hand of a user; one or more power sources carried by the handle body; a light source assembly carried by the handle body and powered by the one or more power sources; a connection section for mechanically connecting the fiber optic laryngoscope blade to the laryngoscope handle and optically coupling the light source assembly in the laryngoscope handle to the fiber optics of the fiber optic laryngoscope blade, wherein the light source assembly includes at least two different types of light sources and a light mixing chamber where light emitted from the two different types of light sources mix to create a combined, mixed light that is transmitted to the fiber optics of the fiber optic laryngoscope blade for emission there from.

One or more implementations of the aspect of the invention described immediately above includes one or more of the following: the light mixing chamber where light emitted from the two different types of light sources mix is a mirrored chamber; the at least two different types of light sources include one or more white light sources and one or more UV light sources; and/or the at least two different types of light sources include a single white light LED and a single UV light LED.

Another aspect of the invention involves a method of using the laryngoscope handle comprising mechanically and optically coupling the fiber optic laryngoscope blade and fiber optics to the connection section of the laryngoscope handle to form a laryngoscope; actuating the light source assembly; mixing light emitted from the two different types of light sources to create a combined, mixed light in the light mixing chamber; transmitting the mixed light from the laryngoscope handle to the fiber optics of the fiber optic laryngoscope blade; and emitting the mixed light from the fiber optics of the fiber optic laryngoscope blade.

A further aspect of the invention involves a method of performing direct laryngoscopy comprised of using the laryngoscope to lift a patient's tongue and mandible for at least one of locating and viewing a foreign object in the patient; emitting the mixed light from the fiber optics to prompt a visible illumination effect in the patient's epiglottis and vocal cords resulting from absorption of some or all of the ultraviolet light by tissues in the patient, providing a back light from phosphorus reactions, and allowing a reaction with a foreign body in the patient; and locating the foreign object in the patient.

A still further aspect of the invention involves performing direct laryngoscopy comprised of using the laryngoscope to lift a patient's tongue and mandible for viewing the vocal cords adjacent the larynx and to aid in the insertion of an endotracheal tube past the vocal cords; emitting the mixed light from the fiber optics to prompt a visible illumination effect in the patient's epiglottis and vocal cords resulting from absorption of some or all of the ultraviolet light by tissues in the patient, providing back light from phosphorus reaction, and making the patient's vocal cords at the glottis visible and identifying a pathway for the endotracheal tube to the trachea; and performing endotracheal intubation in the patient by inserting the endotracheal tube into the patient's mouth, between the patient's visible vocal cords into the larynx, and then into the trachea.

Further objects and advantages will be apparent to those skilled in the art after a review of the drawings and the detailed description of the preferred embodiments set forth below.

DETAILED DESCRIPTION OF PREFERRED EMBODIMENTS

Figure 1:
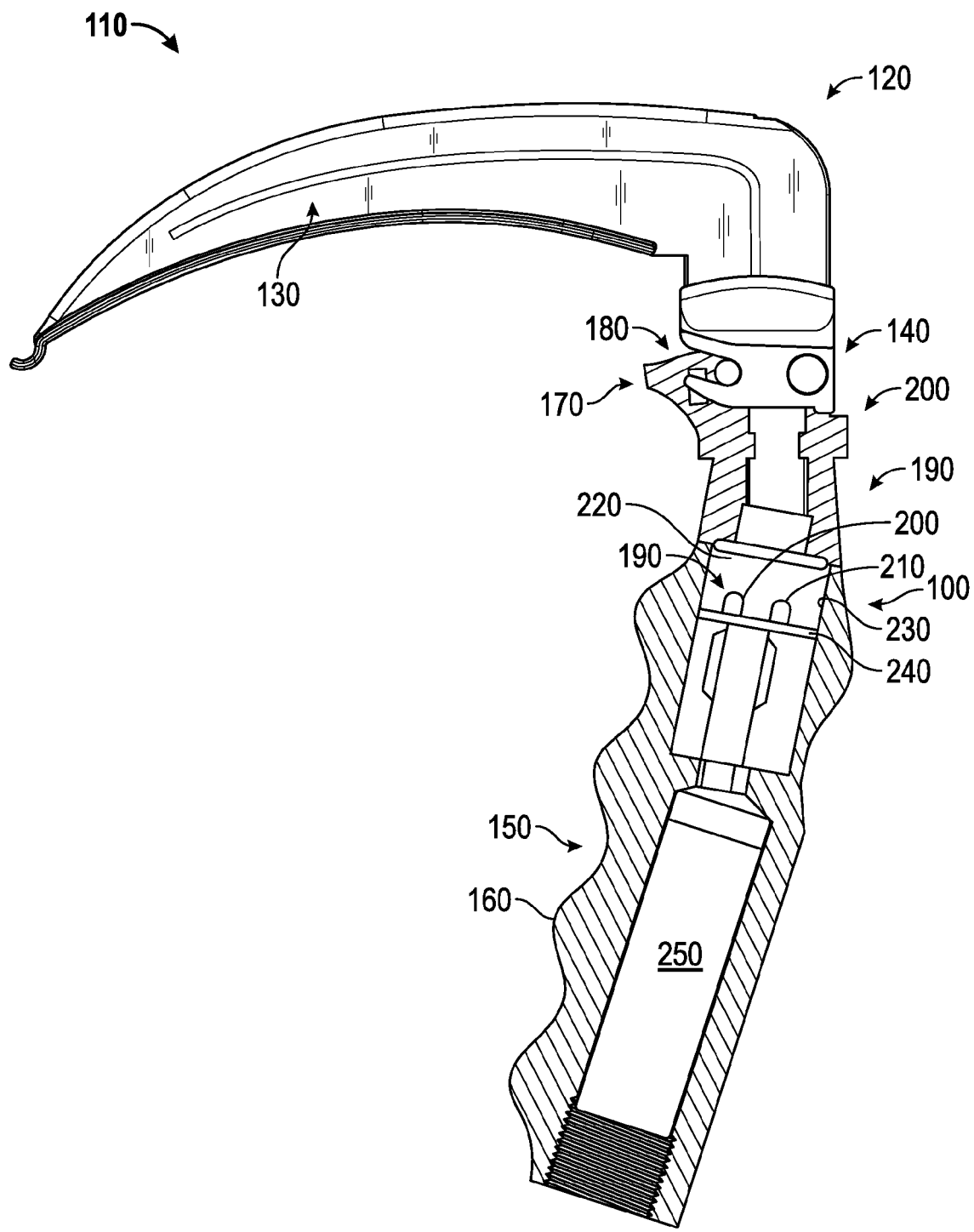
FIG. 1 is a partial side perspective view and partial cross-sectional view of a laryngoscope with a fiber optic laryngoscope blade shown in side perspective view and an embodiment of a laryngoscope handle shown in cross-sectional view.

With reference to FIG. 1, an embodiment of a laryngoscope handle 100 for a laryngoscope 110 will be described. In the embodiment shown, an illumination device in the form of a fiber optic laryngoscope blade 120 is connected to the laryngoscope handle 100. The laryngoscope blade 120 (e.g., curved Macintosh blade, straight Miller/Robertshaw blade, or other type of blade) carries fiber optics (e.g., fiber optic light tube) 130. The fiber optic light tube 130 is optically coupled to a connection section 140, where the laryngoscope blade 120 connects to the laryngoscope handle 100. In alternative embodiments, other types of illumination devices other than a laryngoscope blade 120 are used and other illumination sources other than a laryngoscope handle 100 are used.

In this embodiment, the laryngoscope handle 100 has a curved, ergonomic laryngoscope handle body with a series of finger grip indents 150 on an inner surface 160. The laryngoscope handle 100 has a connection section 170 at an upper end 180 of an upper portion 190 with connection mechanism 200 for mechanically and optically coupling the connection section 140 of the laryngoscope blade 120 and the connection section 170 of the laryngoscope handle 100. The connection mechanism 200 may include a switch therein (e.g., an electrically conductive ball contact in connection portion(s) 140 and/or 170 that contact each other to close circuit) that is automatically operated when the connection sections 140, 170 are connected for actuating an illumination source system 190 discussed below. For example, the illumination source system 190 is automatically placed in communication with one or more power sources 250 when the laryngoscope blade 120 is assembled or clicked together with the upper part of the laryngoscope handle 100, and are automatically turned off when the laryngoscope blade 120 is released or disassembled from the upper part of the laryngoscope handle 100 for storage when not in use, for example when the laryngoscope blade 120 is unlocked/unlatched from the upper part of the laryngoscope handle 100. Alternatively or additionally, the laryngoscope handle 100 may include a manual switch for turning the illumination source system 190 on, off, and/or otherwise controlling the illumination source system 190 (e.g., switching to at least one of an "off" condition, an "on" condition in which both UV and white light is emitted, a UV light only condition, and a white light only condition).

Adjacent to the connection section is an illumination source system 190. The illumination source system 190 includes one or more white light illumination sources 200, preferably one or more white light LED(s). In alternative embodiments, the one or more white light illumination sources 200 include, but are not limited to, a white halogen light and/or a white incandescent light. The illumination source system 190 also includes one or more ultra violet (UV) light illumination sources 210, preferably one or more UV LED(s). The one or more UV light illumination sources 210 emit long wave UVA radiation and little visible light. The one or more UV light illumination sources 210 emit electromagnetic radiation that is in the soft, near ultraviolet range. The one or more UV light illumination sources 210 prompt the visible effects of fluorescence and phosphorescence with respect to the patient's vocal cords and the glottis, which is the space between the vocal cords, during laryngoscopy. In one embodiment, the one or more UV light illumination sources 210 emit electromagnetic radiation including a wavelength in the range of 315 to 400 nm, without emitting substantial electromagnetic radiation including a wavelength outside of the range of 300 to 450 nm. In another embodiment, the one or more UV light illumination sources 210 emit electromagnetic radiation including a wavelength of 385-395 nm. The illumination source system 190 may include a chamber 220 with mirrored wall(s) 230. The chamber 220 may be cone-shaped or have another configuration to enhance the reflection and emission of light from the illumination source system 190. The illumination sources 200, 210 may be connected to a printed circuit board (PCB) 240, which is electrically coupled to and powered by one or more power sources 250 (e.g., one or more rechargeable batteries, one or more disposable batteries, one or more dry cell batteries such as one or more lithium ion batteries).

An exemplary method of performing a medical procedure, and, in particular, an endotracheal intubation using the laryngoscope handle 100 and laryngoscope blade 120 of the laryngoscope is described below. The illumination source system 190 of the laryngoscope handle 100 is actuated (e.g., when the laryngoscope 110 is clicked together/assembled). This causes the one or more white light illumination sources 200 and the one or more UV light illumination sources 210 in the laryngoscope handle 100 to emit, respectively, white and UV light, which are mixed in the chamber 220 of the handle 100, resulting in a mixed, combination of white and UV light, which is transmitted to the fiber optic light tube 130. At a distal end of the fiber optic light tube 130, the combination of white and UV light is emitted distally from a distal end portion of the laryngoscope blade 120. The laryngoscope blade 120 is inserted into a patient's mouth and behind the patient's tongue and mandible. By gripping the handle 100 with one's hand, the tongue and mandible are lifted for viewing the vocal cords adjacent the larynx and to aid in the insertion of an endotracheal tube past the vocal cords. The black light of the combination black and UV light emitted from the fiber optic light tube 130 prompts the visible effects of fluorescence and phosphorescence with respect to the patient's vocal cords and the glottis, making the patient's vocal cords at the glottis visible either directly by the eyes of the medical provider or via a scope of the endotracheal tube (or via an electronic display). The black light causes vocal cords or vocal folds to naturally fluoresce, clearly identifying pathway to the trachea. The white light in combination with UV light provides general illumination (e.g., of the interior of the mouth and back of the patient's throat). This brightness of the white light is bright enough to provide general illumination (e.g., of the interior of the mouth and back of the patient's throat) while not being so bright as to overtake the effects of the UV light. The mixed UV and white light combination lighting produces "near-3D optimization of viewing area, causing airway structures to stand out via precision-shadowing effect. The UV and white light wavelength mix dramatically improves discrimination of tissues, field of view, reduces glare and creates better depth perception in the airway. The endotracheal tube is inserted into the patient's mouth, between the patient's visible vocal cords into the larynx, and then into the trachea of the patient in a usual manner. A stylet of the endotracheal tube may be used to shape the scope/endotracheal tube to the individual anatomy/pathology of the patient. In an embodiment of the laryngoscope handle 100 including a manual switch/controller, the respective light sources 200, 210 may be individually/selectively actuated or deactivated (e.g., to cause only UV light to be emitted, only white light to be emitted, no light to be emitted, and/or a mixed, combined UV and white light to be emitted) so that optimal viewing of the vocal cords occurs. The medical provider may prefer to use the UV light condition and/or the white light condition, depending on external lighting conditions, the individual anatomy/pathology of the patient, the patient's condition, and other factors.

In an alternative exemplary method, which is described in U.S. patent application U.S. Patent Application No. 13/328, 499, which is incorporated by reference herein, the laryngoscope 110 is used to assist in removal of an obstruction or foreign object from a patient's trachea.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in the following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items e present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

We claim:

1. A laryngoscope handle for use with a fiber optic laryngoscope blade including fiber optics, comprising:
 a laryngoscope handle body configured to be gripped by a handle of a user;
 one or more power sources carried by the handle body;
 a light source assembly carried by the handle body and powered by the one or more power sources;
 a connection section for mechanically connecting the fiber optic laryngoscope blade to the laryngoscope handle and optically coupling the light source assembly in the laryngoscope handle to the fiber optics of the fiber optic laryngoscope blade;
 wherein the light source assembly includes at least two different types of light sources and a light mixing chamber where light emitted from the two different types of light sources mix to create a combined, mixed light that is transmitted to the fiber optics of the fiber optic laryngoscope blade for emission there from wherein the light source assembly is spaced proximal of the connection section and the light mixing chamber is a mirrored chamber.

2. The laryngoscope handle of claim 1, wherein the at least two different types of light sources include one or more white light sources and one or more UV light sources.

3. The laryngoscope handle of claim 1, wherein the at least two different types of light sources include a single white light LED and a single UV light LED.

4. A method of using the laryngoscope handle of claim 1, comprising:
 mechanically and optically coupling the fiber optic laryngoscope blade and fiber optics to the connection section of the laryngoscope handle to form a laryngoscope;
 actuating the light source assembly;
 mixing light emitted from the two different types of light sources to create a combined, mixed light in the light mixing chamber;
 transmitting the mixed light from the laryngoscope handle to the fiber optics of the fiber optic laryngoscope blade;
 emitting the mixed light from the fiber optics of the fiber optic laryngoscope blade.

5. The method of claim 4, further including performing direct laryngoscopy, comprising:
 using the laryngoscope to lift a patient's tongue and mandible for at least one of locating and viewing a foreign object in the patient;
 emitting the mixed light from the fiber optics to prompt a visible illumination effect in the patient's epiglottis and vocal cords resulting from absorption of some or all of the ultraviolet light by tissues in the patient, providing a back light from phosphorus reactions, and allowing a reaction with a foreign body in the patient; and
 locating the foreign object in the patient.

6. The method of claim 4, further including performing direct laryngoscopy, comprising:
 using the laryngoscope to lift a patient's tongue and mandible for viewing the vocal cords adjacent the larynx and to aid in the insertion of an endotracheal tube past the vocal cords;
 emitting the mixed light from the fiber optics to prompt a visible illumination effect in the patient's epiglottis and vocal cords resulting from absorption of some or all of the ultraviolet light by tissues in the patient, providing back light from phosphorus reaction, and making the patient's vocal cords at the glottis visible and identifying a pathway for the endotracheal tube to the trachea; and
 performing endotracheal intubation in the patient by inserting the endotracheal tube into the patient's mouth, between the patient's visible vocal cords into the larynx, and then into the trachea.

7. A method of using a laryngoscope, comprising:
 providing a laryngoscope comprising a laryngoscope handle and a fiber optic laryngoscope blade including fiber optics, the laryngoscope handle including one or more power sources, a light source assembly carried by the handle body and powered by the one or more power sources, a connection section for mechanically connecting the fiber optic laryngoscope blade to the laryngoscope handle and optically coupling the light source assembly in the laryngoscope handle to the fiber optics of the fiber optic laryngoscope blade, wherein the light source assembly is spaced proximal of the connection section and the light source assembly includes a mirrored light mixing chamber;
 mechanically and optically coupling the fiber optic laryngoscope blade and fiber optics to the connection section of the laryngoscope handle to form a laryngoscope;
 actuating the light source assembly;
 transmitting mixed light including UV light from the light source assembly through the fiber optics of the fiber optic laryngoscope blade;
 emitting the mixed light from the fiber optics of the fiber optic laryngoscope blade.

8. The method of claim 7, further including performing direct laryngoscopy, comprising:
 using the laryngoscope to lift a patient's tongue and mandible for at least one of locating and viewing a foreign object in the patient;
 emitting the mixed light from the fiber optics to prompt a visible illumination effect in the patient's epiglottis and vocal cords resulting from absorption of some or all of the ultraviolet light by tissues in the patient, providing a back light from phosphorus reactions, and allowing a reaction with a foreign body in the patient; and
 locating the foreign object in the patient.

9. The method of claim 8, wherein the mixed light is a mixture of white light and UV light.

10. A laryngoscope handle for use with a fiber optic laryngoscope blade including fiber optics, comprising:
- a laryngoscope handle body configured to be gripped by a handle of a user;
- one or more power sources carried by the handle body;
- a light source assembly carried by the handle body and powered by the one or more power sources;
- a connection section for mechanically connecting the fiber optic laryngoscope blade to the laryngoscope handle and optically coupling the light source assembly in the laryngoscope handle to the fiber optics of the fiber optic laryngoscope blade;
- wherein the light source assembly includes at least two different types of light sources and a light mixing chamber where light emitted from the two different types of light sources mix to create a combined, mixed light that is transmitted to the fiber optics of the fiber optic laryngoscope blade for emission there from,
- wherein the light source assembly is spaced from the connection section and the at least two different types of light sources include one or more white light sources and one or more UV light sources.

11. A laryngoscope handle for use with a fiber optic laryngoscope blade including fiber optics, comprising:
- a laryngoscope handle body configured to be gripped by a handle of a user;
- one or more power sources carried by the handle body;
- a light source assembly carried by the handle body and powered by the one or more power sources;
- a connection section for mechanically connecting the fiber optic laryngoscope blade to the laryngoscope handle and optically coupling the light source assembly in the laryngoscope handle to the fiber optics of the fiber optic laryngoscope blade;
- wherein the light source assembly includes at least two different types of light sources and a light mixing chamber where light emitted from the two different types of light sources mix to create a combined, mixed light that is transmitted to the fiber optics of the fiber optic laryngoscope blade for emission there from,
- wherein the light mixing chamber is a mirrored chamber and the at least two different types of light sources include one or more white light sources and one or more UV light sources.

12. A method of using a laryngoscope, comprising:
- providing a laryngoscope comprising a laryngoscope handle and a fiber optic laryngoscope blade including fiber optics, the laryngoscope handle including one or more power sources, a light source assembly carried by the handle body and powered by the one or more power sources, a connection section for mechanically connecting the fiber optic laryngoscope blade to the laryngoscope handle and optically coupling the light source assembly in the laryngoscope handle to the fiber optics of the fiber optic laryngoscope blade, wherein the light source assembly is spaced from the connection section and the light source assembly has at least two different types of light sources including one or more white light sources and one or more UV light sources;
- mechanically and optically coupling the fiber optic laryngoscope blade and fiber optics to the connection section of the laryngoscope handle to form a laryngoscope;
- actuating the light source assembly;
- transmitting mixed light including UV light from the light source assembly through the fiber optics of the fiber optic laryngoscope blade;
- emitting the mixed light from the fiber optics of the fiber optic laryngoscope blade.

13. A method of using a laryngoscope, comprising:
- providing a laryngoscope comprising a laryngoscope handle and a fiber optic laryngoscope blade including fiber optics, the laryngoscope handle including one or more power sources, a light source assembly carried by the handle body and powered by the one or more power sources, a connection section for mechanically connecting the fiber optic laryngoscope blade to the laryngoscope handle and optically coupling the light source assembly in the laryngoscope handle to the fiber optics of the fiber optic laryngoscope blade, wherein the light source assembly includes a mirrored light mixing chamber and the light source assembly has at least two different types of light sources including one or more white light sources and one or more UV light sources;
- mechanically and optically coupling the fiber optic laryngoscope blade and fiber optics to the connection section of the laryngoscope handle to form a laryngoscope;
- actuating the light source assembly;
- transmitting mixed light including UV light from the light source assembly through the fiber optics of the fiber optic laryngoscope blade;
- emitting the mixed light from the fiber optics of the fiber optic laryngoscope blade.

* * * * *